(12) United States Patent
Seshimoto et al.

(10) Patent No.: US 6,328,167 B1
(45) Date of Patent: Dec. 11, 2001

(54) BLOOD FILTER CARTRIDGE

(75) Inventors: Osamu Seshimoto; Takaki Arai; Kenichiro Yazawa, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/473,497

(22) Filed: Dec. 28, 1999

(30) Foreign Application Priority Data

Dec. 28, 1998 (JP) .................................................. 10-372704

(51) Int. Cl.[7] .................................................. B01D 29/00
(52) U.S. Cl. .......................... 210/456; 210/503; 210/505
(58) Field of Search ................................ 210/435, 456, 210/500.21, 483, 488, 489, 490, 503, 505, 506, 507, 508, 457; 422/101, 102

(56) References Cited

U.S. PATENT DOCUMENTS

| Re. 35,225 | * | 4/1996 | Herweck et al. | 604/321 |
|---|---|---|---|---|
| 4,987,085 | * | 1/1991 | Allen et al. | 436/169 |
| 5,266,219 | * | 11/1993 | Pall et al. | 210/767 |
| 5,979,669 | * | 11/1999 | Kitajima et al. | 210/455 |
| 5,996,811 | * | 12/1999 | Kitajima et al. | 210/488 |
| 6,045,699 | * | 4/2000 | Yazawa et al. | 210/637 |

* cited by examiner

Primary Examiner—John Kim
(74) Attorney, Agent, or Firm—Reed Smith LLP

(57) ABSTRACT

The blood filter cartridge can filter almost total volume of drawn blood efficiently which comprises a blood filtering material and a holder containing the blood filtering material, wherein the holder is provided with a blood reservoir which connects with an inflow side of the blood filtering material and a filtrate receiver which connects with an outflow side of the blood filtering material.

6 Claims, 3 Drawing Sheets

BLOOD FILTER CARTRIDGE

BACKGROUND OF THE INVENTION

This invention relates to a blood filter cartridge for the preparation of a plasma or serum sample from whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter cartridge composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter cartridge composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

The inventors further developed various blood filter cartridges, and their patent applications were made (Japanese Patent KOKAI 10-227788, 10-185909, 10-185780, etc.)

However, since the above blood filter cartridges are of a type of attaching a suction nozzle to the blood inlet and sucking blood from a blood collecting tube, a part of blood essentially remains in the blood collecting tube and the suction nozzle without filtered. As a result, the volume of drawn blood increases to add a burden to a person who takes a medical inspection. Particularly, in the case of clinical assay using a dry analytical element, although analysis of plural items can be achieved by using about 100 to 500 µl plasma, the volume of drawn blood, in general, exceeds 10 ml.

SUMMARY OF THE INVENTION

An object of the invention is to provide a blood filter cartridge which can prepare a plasma or serum sample from a mall volume of blood efficiently.

The inventors investigated eagerly in order to solve the above problems, and found that, by the conventional system, blood inevitably remains in the blood collecting tube due to sucking blood from the tube, and moreover, remains in the suction nozzle due to the slender shape of the blood collecting tube which increases the lift from the blood level in the tube to the blood filter cartridge.

Thereupon, they devised to add a blood reservoir to the blood filter cartridge, and succeeded in filtering almost the total volume of drawn blood by pouring the blood drawn by a blood drawing syringe, and thereby decreasing the volume of drawn blood sharply.

Thus, the present invention provides a blood filter cartridge which comprises a blood filtering material and a holder containing the blood filtering material, wherein the holder is provided with a blood reservoir which connects with an inflow side of the blood filtering material and a filtrate receiver which connects with an outflow side of the blood filtering material.

Figure 1:
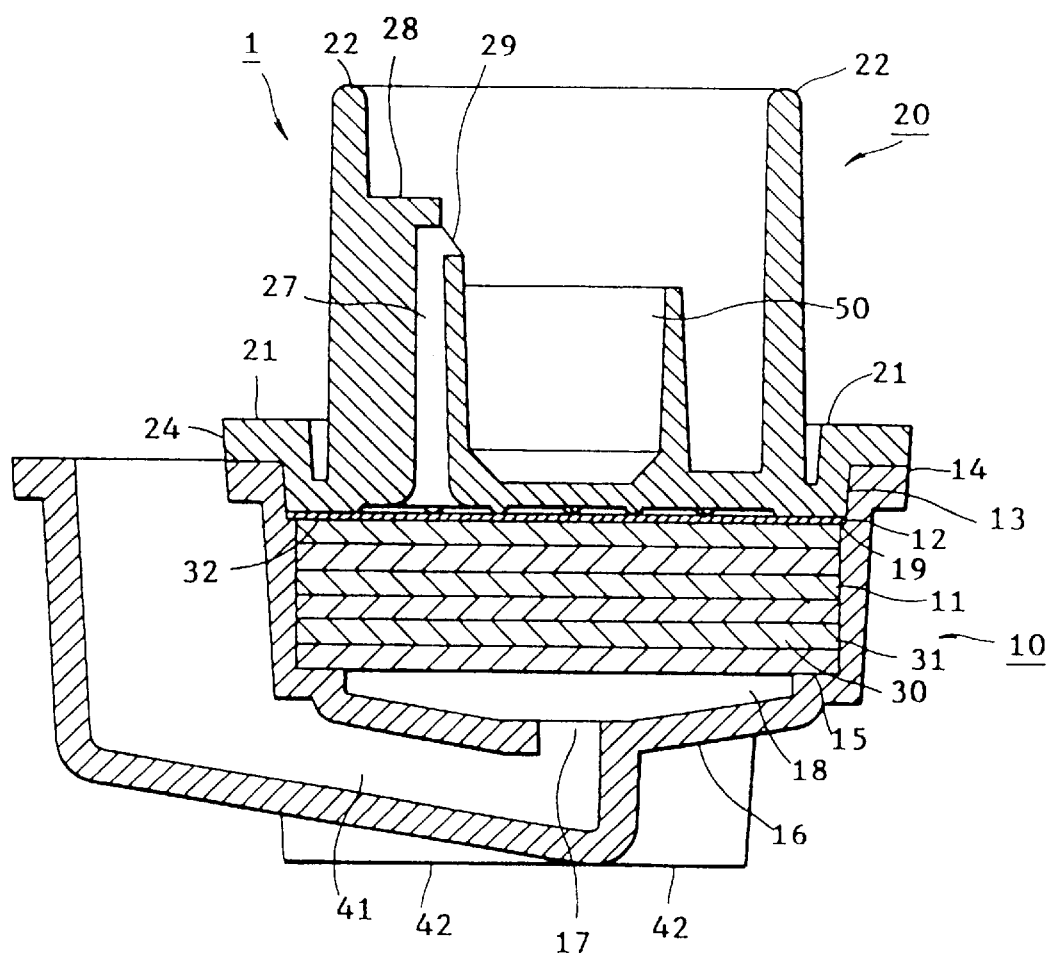
FIG. 1 is a longitudinal section of a blood filter cartridge of the invention.

1 . . . Blood Filter Cartridge
10, 60 . . . Holder body
11, 63 . . . Glass fiber filter chamber (blood filter chamber)
12, 64 . . . Microporous membrane chamber (blood filter chamber)
13 . . . Inclined portion
14 . . . Flange
15 . . . Glass fiber filter-placing portion
16 . . . Funnel-shaped disc portion
17 . . . Blood inlet
18 . . . Space
19 . . . Step portion
20, 67 . . . Cap
21 . . . Outer wall
22 . . . Inner wall
24 . . . Flange
25 . . . Rib
26 . . . Projection
27 . . . Filtrate passage
28 . . . Pent roof
29 . . . Filtrate outlet
30 . . . Blood filtering material
31 . . . Glass fiber filter
32 . . . Polysulfone microporous membrane
40, 61 . . . Blood reservoir
41 . . . Passage
42 . . . Leg
50, 70 . . . Filtrate receiver
65, 66 . . . Perforated plate

DETAILED DESCRIPTION OF THE INVENTION

Although the type of the blood filtering material is not limited, in the filtering material of the invention, it is thought that the filter material to be used does not trap blood cells only by the surface, but catches to remove blood cells gradually by entangling at first large blood cell components and then smaller blood cell components in the space structure with permeating in the thickness direction in total of the filtering material, called the volumetric filtration or depth filtration. Preferable blood filtering material are glass fiber filter, aggregate of extra fine fibers, three dimensional porous body, and the like, and a combination of glass fiber filter or aggregate of extra fine fibers and microporous membrane is particularly preferred.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 µm preferably 1 to 5 µm. By treating the surface of glass fiber with hydrophilic polymer as disclosed in Japanese Patent KOKAI Nos. 2-208676, 4-208856, filtration proceeds more fast and smoothly. Lectin or other reactive reagent or modifier may be incorporated into glass fiber, or glass fiber may be treated therewith. Two or more glass fiber filters may be superimposed.

As the extra fine fibers forming the aggregate of extra fine fibers, there are organic extra fine fibers and metal fibers. Preferable organic extra fine fibers are made of polyester, polypropylene, polyamide, polyethylene, cellulose or the like, and also include carbon fibers. Metal fibers are made of aluminum, copper, gold or the like. A suitable size (diameter) of the fiber is 0.2 to 2.5 µm, preferably 0.3 to 2.3 µm, more preferably 0.4 to 2.2 µm, on average.

The aggregate of extra fine fibers is produced by spinning polyester, polypropylene, polyamide, polyethylene or the like by an ordinary spinning method, such as melt blow (Japanese Patent KOKAI 9-143081, 10-211277, etc.). It is possible to obtain plasma or serum containing blood cells in only a small amount without hemolysis and being suitable for clinical assay by the above blood filtering material.

Optionally, the surface of the fibers can be modified, e.g. by the deposition of platinum or carbon or coating with a hydrophilic polymer membrane, such as gelatin or polyvinyl pyrrolidone.

The form of the aggregate of extra fine fibers is woven fabric, knitted fabric, nonwoven fabric, floe in irregular form, bundle of parallel fibers, or the like. A suitable bulk density is about 0.05 to 0.6 g/cm$^3$, preferably about 0.08 to 0.5 g/cm$^3$.

Since blood cell components are trapped mainly by the entangled portions of the extra fine fibers, a preferable void volume is great in order that filtration proceeds efficiently. As an indicator corresponding to void volume or filtrate volume of plasma, the water permeation speed mentioned previously is suitable. The aggregates of extra fine fibers particularly suitable for plasma separation are having a water permeation speed of about 1.0 to 1.3 ml/sec.

The size of the aggregate of extra fine fibers can be set according to the volume of blood sample to be supplied or the volume of blood plasma necessary for assays. For example, discs of the aggregate of extra fine fibers about 20 mm in diameter are stacked in a thickness of about 2 to 10 mm.

The three dimensional porous bodies suitable for the blood filter cartridge are disclosed in Japanese Patent KOKAI 10-185910, and has a mean poro size of 5 to 50 µm.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, the aggregate of extra fine fibers or the three dimensional porous body, and is 0.2 µm or more, preferably about 0.3 to 5 µm, more preferably about 0.5 to 4.5 µm, particularly preferably about 1 to 3 µm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc. The surface of the membrane may be hydrolyzed or may be rendered hydrophilic by a hydrophilic polymer or an activating agent.

Preferable microporous membranes are polysultone membrane, cellulose acetate membrane, cellulose nitrate membrane, hydrophilic polytetrafluoro ethylene membrane, polyamide membrane and the like, and particularly preferred one is polysulfone membrane. In the blood filtering material of the invention, the glass fiber filter, the aggregate of extra fine fibers and the three dimensional porous body are located on the blood inlet side and the microporous membrane is located on the filtrate outlet side. The most preferable blood filtering material is a combination of the glass fiber filter or the aggregate of extra fine fibers and polysulfone membrane laminated in this order from the blood inlet side.

Respective layers may be integrated by joining each other using partially disposed (e.g. spots) adhesive, according to disclosures in Japanese Patent KOKAI Nos. 62-138756-8, 2-105043, 3-16651, etc.

A suitable thickness of the glass fiber filter varies according to the plasma volume to be recovered and density (void content) and area of the glass fiber filter. A necessary amount of plasma for analyzing plural items using dry analytical elements is 100 to 500 µl. In practical viewpoint, a glass fiber filter having a density of about 0.02 to 0.2 g/cm$^3$ and an area of 1 to 5 cm$^2$ is suitable. In this case, a suitable thickness of the glass fiber filter is about 1 to 10 mm, preferably about 2 to 8 mm, more preferably about 4 to 6 mm. The above thickness can be made by superposing 2 to 10 sheets, preferably 3 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

The blood filtering material is placed in a holder having a blood inlet and a plasma outlet. The holder is, in general, formed of a body containing the blood filtering material and a cap, and each of them is provided with at least one aperture. One is used as the blood inlet, and the other is used as the filtrate outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which contains the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. An actual volume is set depending on the necessary amount of plasma or serum, and is about 0.5 to 2.5 ml, usually about 0.6 to 2.2 ml.

Besides, it is preferable that the periphery of the blood filtering material is closely fitted to the wall of the filter chamber so as not to form a bypass of whole blood without passing the filtering material.

The blood filter cartridge is made into a closed structure except the blood inlet and the plasma outlet by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

To the holder, the blood reservoir and the filtrate receiver are provided.

The blood reservoir stores blood being fed to the blood filtering material, and is connected to a blood inlet directly or through a passage. The attaching position of the blood reservoir is any position of the side wall, the top or the bottom of the holder. However, even when the blood reservoir is attached to the bottom, it is preferable to arrange the position and the capacity capable of being impregnated into a part of the blood filtering material by self weight of the blood poured into the blood reservoir. Therefore, the level of a prescribed volume of blood poured in the reservoir is made upper than the underside of the blood filtering material presumed without permeating blood into the blood filtering material. The shape of the blood reservoir is not restricted. A suitable capacity of the blood reservoir is, in the case of the preparation of a sample for dry analysis, about 0.2 to 5 ml, usually about 0.5 to 2 ml. When the blood reservoir is connected to the blood inlet through a passage, the volume of the passage is incorporated into the capacity. When there is a space on the inlet side of the blood filtering material, the space is also incorporated into the capacity. In the case that there is a space under the blood filtering material where the blood inlet is provided at the periphery, it is preferable to provide a partition plate having a hole at the center or small holes over the whole area so that bubbles upon the finish of blood filtration pass the hole or small holes to be spread over the whole body of the blood filtering material.

The filtrate receiver receives plasma or serum which is the filtrate discharge from the filtrate outlet, and the filtrate outlet is located above the liquid level of the filtrate receiver. The filtrate outlet may be provided on the upper part of the side wall of the filtrate receiver or a pipe standing on the inside of the filtrate receiver. The filtrate receiver is made into various shapes in connection with various factors, such as the relation to the position of sucking analytical sample, the relation to the blood filtering chamber, the relation to optional other parts, and the like, and, in general, cylindrical or square. The bottom of the filtrate receiver is flat, funnel-shaped, round or the like. The volume of the filtrate receiver is, in the case of preparation of analytical sample for dry analysis, about 100 to 900 µl, usually about 200 to 600 µl, and has a depth of about 3 to 12 mm and a width (diameter a side length) of about 5 to 11 mm. As to the position of the position of the filtrate outlet, the underside of the filtrate outlet is located higher than the designed liquid level of the filtrate receiver by about 0.5 to 5 mm, usually about 1 to 2 mm. Although the volume of filtrate varies according to the hematocrit value of blood, the designed liquid level is of filtering blood having a hematocrit value of 20 to 60%. The filtrate receiver may be integrated with or separated from the holder.

Heretofore, the blood filter cartridge is explained about the type of introducing blood from the underside of the blood filtering material and discharging the filtrate from the upside. However, the blood filter cartridge of the invention may be an opposite type, i.e. feeding blood from the upside of the blood filtering material and discharging the filtrate from the underside.

EXAMPLES

Example 1

Figure 2:
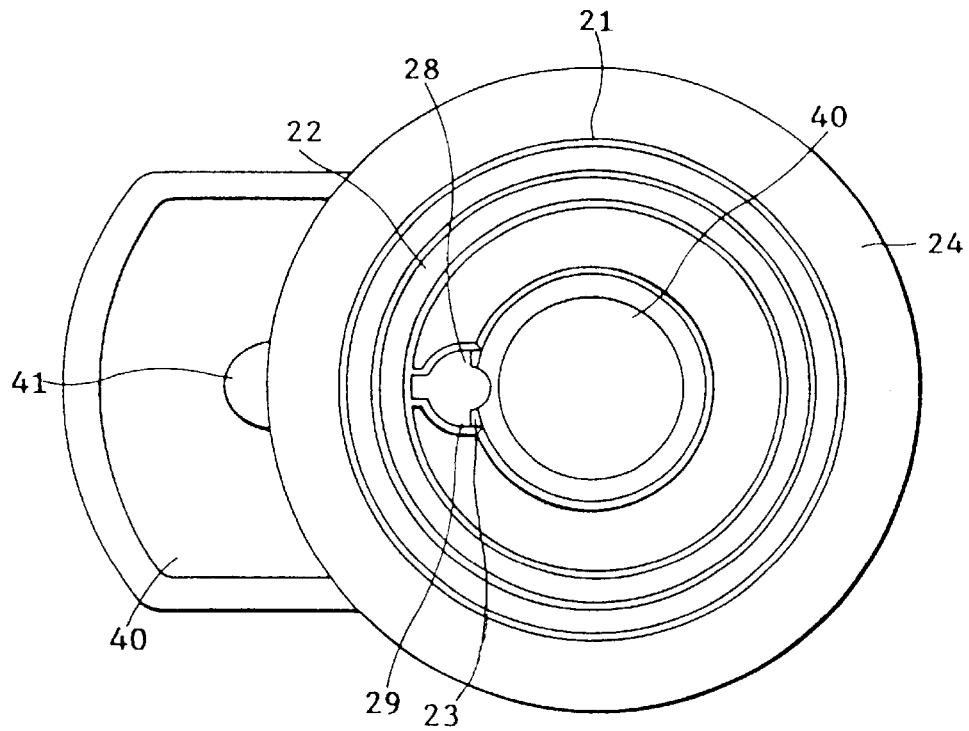
FIG. 2 is a plan view thereof.
Figure 3:
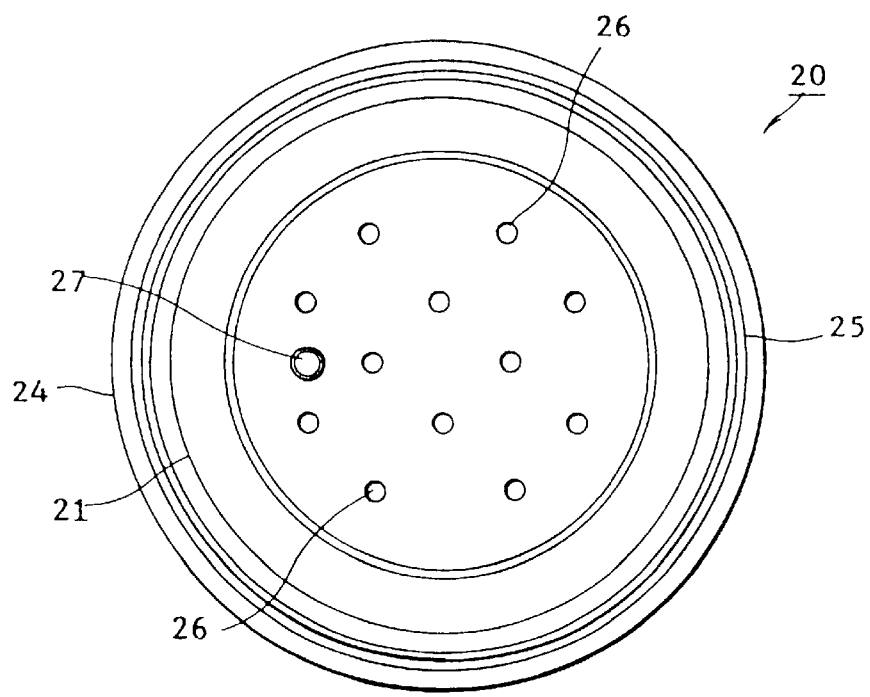
FIG. 3 is a bottom view of the cap of the cartridge.

A blood filter cartridge of the inventors is illustrated in FIGS. 1–3. FIG. 1 is a longitudinal section of the blood filter cartridge in the assembled state, FIG. 2 is a plan view thereof, and FIG. 3 is a bottom view of the cap which constitutes the blood filter cartridge.

The blood filter cartridge is, as shown in FIG. 1, composed of a holder 1 consisting of a holder body 10 and a cap 20 and blood filtering material 30 consisting of a glass fiber filter 31 and a microporous membrane 32.

The holder body 10 is made of high-impact polystyrene resin, and has a glass fiber filter chamber 11 for containing the glass fiber filter 31 and a microporous membrane chamber 12 for containing a polysulfone microporous membrane as the microporous membrane 32 above the glass fiber filter chamber 11. The microporous membrane chamber 12 has a diameter greater than the glass fiber filter chamber, and the periphery of the microporous membrane 32 is nipped by the step portion 19 formed on the boundary between the glass fiber filter chamber 11 and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A circle hole is provided as the blood inlet 17 at the center of the funnel-shaped portion 16. The glass fiber filter-placing portion 15 also functions as a spacer which separates the glass fiber filter 31 from the bottom and forms a space 18 for spreading the liquid to be filtered over the whole surface of the glass fiber filter 31.

The holder body 10 is provided with a messtin-shaped blood reservoir 40 on the left side in FIG. 1, and a passage 41 connecting the blood reservoir 40 to the blood inlet 17 gradually descends from the center of the bottom of the reservoir 40 toward the blood inlet 17. Three legs 42 are formed on the bottom of the holder body 10 radially at regular intervals.

The cap 20 has an outer wall 21 and an inner wall 22 formed concentrically and a filtrate receiver 50 for storing the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined 13 in a sealed state. A flange 24 is formed outward at the periphery of the outer wall 21, and the flange 24 is bonded to the flange 14 of the holder body 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projection 26 prevent the polysulfone microporous membrane 32 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, and the periphery of the large half circle conforms to the periphery of the filtrate passage 27. The discharge port 29 of the filtrate is provide obliquely at the upper end of the filtrate passage 27, and has the form of a lower half ellipse. Screens (opposite faces) 23 are formed on both sides from the filtrate outlet 29 to the upper edge of the filtrate receiver 50 in order to prevent scattering of filtrate.

The above blood filter cartridge has a diameter of the glass fiber filter chamber 11 of 20. 1 mm and a depth thereof of 5.9 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the filtrate receiver 50 of 7.5 mm. The glass fiber filter 31 consists of six lass fiber filter sheets each having a diameter of 20.0 mm and a thickness of 0.91 mm, and the microporous membrane consists of one polysulfone microporous membrane having a diameter of 20.9 mm and a thickness of 150 $\mu$m. The filtrate outlet 29 has a longitudinal diameter of 1.3 mm and a lateral diameter of 1.2 mm. The thickness of the pent roof 28 is 1 mm, and the distance between both screens (the distance of the opposite faces 23) is 2 mm.

Example 2

Figure 4:
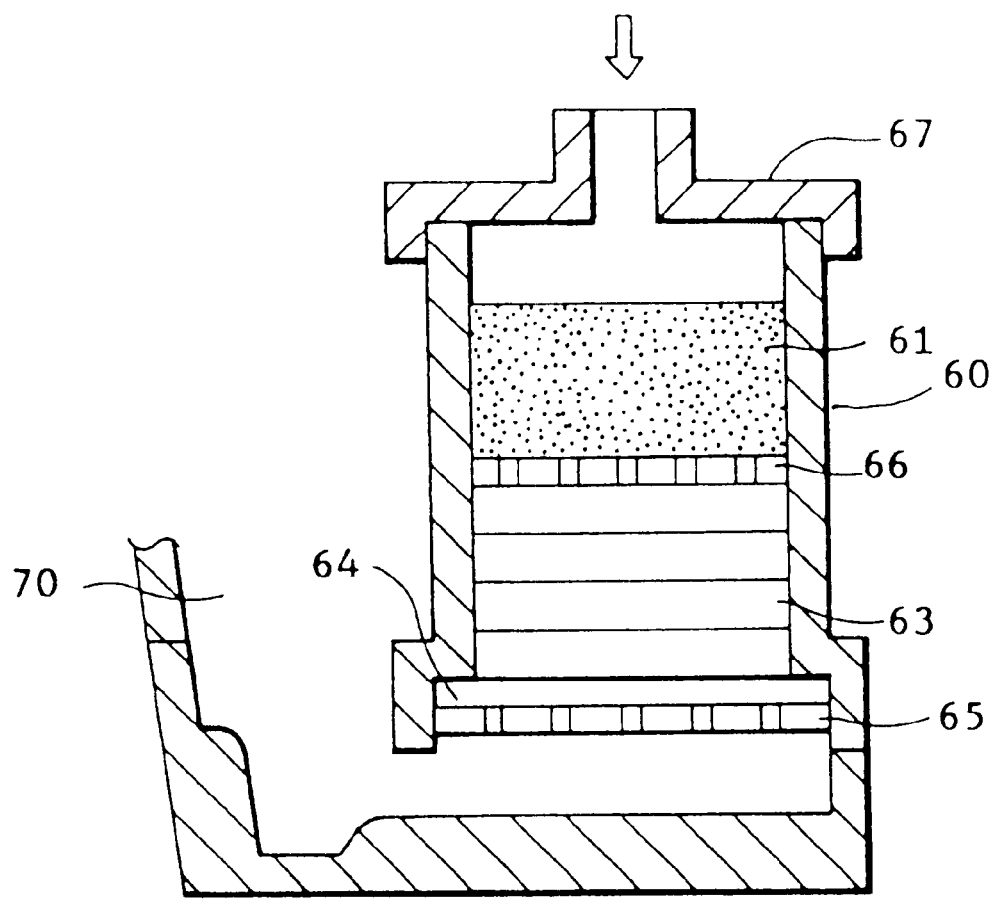
FIG. 4 is a longitudinal section of another blood filter cartridge of the invention.

Another blood filter cartridge of th e invention is illustrated in FIG. 4.

The blood filter cartridge is in pressurizing type, composed of a cylindrical holder body 60 and a filtrate receiver 70 provided on the left side of the holder body 60 in FIG. 4.

The upper part of the holder body 60 is a blood reservoir 61, and the lower part is a blood filter chamber. The main part of the blood filter chamber is a glass fiber filter chamber 63, and the underside therefrom is slightly enlarged to form a polystyrene membrane chamber 64. These blood filtering materials are held by perforate d plates 65, 66 so as not to escape therefrom.

A pressure cap 67 is mounted to the upper opening, and the inside of the holder body 60 can be pressurized by pumping air.

The bottom of the holder body 60 is a slope so that the filtrate is streamed into the filtrate receiver 70.

What is claimed is:

1. A blood filter cartridge which filters blood through upflow of the blood and which comprises a blood filtering material and a holder containing the blood filtering material, said holder having sides and a blood reservoir which connects with an inflow side of the blood filtering material and a filtrate receiver which connects with an outflow side of the blood filtering material wherein the blood reservoir is located on a side of the holder and the blood reservoir has an upper edge which is higher than an underside of the blood filtering material.

2. The blood filter cartridge of claim 1 wherein the blood filtering material consists essentially of glass fiber filter and microporous membrane.

3. The blood filter cartridge of claim 1 wherein the blood filtering material comprises an aggregate of extra fine fibers having a fiber diameter of 0.2 to 2.5 $\mu$m.

4. The blood fitter cartridge of claim 1 wherein the blood reservoir is designed so as to stream the blood poured into the blood reservoir to contact the blood filtering material by self weight of the blood.

5. The blood filter cartridge of claim 1 wherein a filter chamber containing the blood filtering material has a volume of 0.5 to 2.5, and the blood reservoir has a capacity of 0.2 to 5 ml.

6. The blood filter cartridge of claim 5 wherein the blood reservoir has a capacity of 0.5 to 2 ml.

* * * * *